United States Patent [19]

Rossi et al.

[11] 4,115,416

[45] Sep. 19, 1978

[54] PROCESS FOR THE MANUFACTURE OF NEW CARBOXYLIC ACIDS

[75] Inventors: Alberto Rossi, Oberwil; Christian Egli, Magden, both of Switzerland

[73] Assignee: Ciba-Geigy AG, Basel, Switzerland

[21] Appl. No.: 721,737

[22] Filed: Sep. 9, 1976

Related U.S. Application Data

[63] Continuation-in-part of Ser. No. 153,804, Jun. 16, 1971, and Ser. No. 576,397, May 9, 1975, which is a continuation-in-part of Ser. No. 153,804, , which is a continuation-in-part of Ser. No. 98,116, Dec. 14, 1970, abandoned.

[30] Foreign Application Priority Data

May 17, 1974 [CH] Switzerland .................... 6786/74
Oct. 28, 1974 [CH] Switzerland .................... 14402/74

[51] Int. Cl.² .................... C07C 69/76; C11C 1/00

[52] U.S. Cl. .................... 260/413; 544/391; 260/293.76; 260/293.8; 260/326.42; 260/410; 544/399; 260/559 B; 560/21; 424/308; 544/59; 544/174; 560/45; 560/59; 562/469; 562/435; 562/452; 562/455; 568/743; 568/731

[58] Field of Search .................... 260/413, 520 C, 473 G; 560/59; 424/308, 318, 317

[56] References Cited

U.S. PATENT DOCUMENTS

| 3,755,603 | 8/1973 | Harrison | 560/59 |
| 4,008,269 | 2/1977 | Diamond | 560/51 |
| 4,035,413 | 7/1977 | Haas et al. | 560/59 |

*Primary Examiner*—Paul J. Killos
*Attorney, Agent, or Firm*—Theodore O. Groeger

[57] ABSTRACT

α-Phenoxyacetic acids, in which the α-position is substituted by an alkyl residue with 5 to 12 carbon atoms and the phenyl residue is substituted by a cycloaliphatic hydrocarbon residue which is unsaturated in the 1-position and is only singly unsaturated, and their esters and amides are useful as hypolipidaemic agents.

15 Claims, No Drawings

PROCESS FOR THE MANUFACTURE OF NEW CARBOXYLIC ACIDS

CROSS REFERENCE TO OTHER APPLICATIONS

This application is a continuation-in-part of our copending applications Ser. No. 153,804, filed June 16, 1971, and Ser. No. 576,397, filed May 9, 1975. The latter application is a continuation-in-part of our continuation-in-part application Ser. No. 153,804, filed June 16, 1971, which in turn is a continuation-in-part of our application Ser. No. 98,116, filed Dec. 14, 1970, now abandoned.

SUMMARY OF THE INVENTION

The present invention relates to new phenoxyacetic acids in which the α-position is substituted by an alkyl residue with 5 to 12 carbon atoms and the phenyl residue is substituted by a cycloaliphatic hydrocarbon residue with is unsaturated in the 1-position and is only singly unsaturated, and their esters and amides, and salts thereof as well as pharmaceutical preparations containing those compounds and a method for the treatment of arteriosclerosis which consist in administering to a warm blooded being such pharmaceutical preparations.

The $C_5$–$C_{12}$-alkyl residue in the α-position of the new compounds is primarily a straight-chain residue; However, it can also be branched. As examples of such a residue there may be mentioned n-pentyl, n-hexyl, n-heptyl, n-nonyl, n-undecyl and n-dodecyl residues, but chiefly n-octyl and n-decyl residues; in addition, 2-n-heptyl, 2-n-octyl, 2-n-nonyl and 2-n-decyl residues may be mentioned.

The cycloaliphatic hydrocarbon residue which is unsaturated in the 1-position and only singly unsaturated can contain several rings, especially two rings, but is primarily a monocyclic residue. Bicyclic residues preferably contain rings with 5–7 ring members which have 1–4, preferably 2, carbon atoms in common. Optionally lower-alkylated 1,2-dehydrodecalinyl-(1) and-(2) residues, 2-bicyclo[2,2,2] octene-(2) residues, 2-bornenyl residues and 2-norbornenyl residues may be mentioned by way of examples.

Monocyclic residues, that is to say 1-cycloalkenyl residues, are primarily residues with 4–12 and preferably 5–8 ring members, such as for example optionally lower-alkylated 1-cyclobutenyl, 1-cyclodecenyl, 1-cyclododecenyl or especially optionally lower-alkylated 1-cyclopentenyl, 1-cyclohexenyl, 1-cycloheptenyl or 1-cyclooctenyl residues.

The phenoxy residue can carry the cycloaliphatic hydrocarbon residue, which is unsaturated in the 1-position, in the ortho-position, but preferably carries it in the meta-position and very particularly in the para-position. The phenyl ring can possess one, two or more further, identical or different subsituents. As substituents there may for example be mentioned; lower alkyl groups, for example those mentioned, halogen atoms, such as fluorine, bromine and especially chlorine atoms, trifluoromethyl groups, nitro groups, amino groups, such as for example di-lower alkylamino groups and acylamino groups, in which the acyl residues are for example lower alkanoyl groups, such as acetyl, propionyl or butyryl groups, or benzoyl groups.

The esters of the new phenoxy- acids are above all those which hydroxyl compounds of formula $R_oOH$, wherein $H_o$ is an aromatic residue or above all a residue of aliphatic character, for example a hydrocarbon residue of aliphatic character, which can be substituted yet further, for example in the aliphatic part by amino groups and/or hydroxyl groups and in an optionally present aromatic ring by lower alkyl residues, for example those mentioned, lower alkoxy groups, especially lower alkoxy groups containing the lower alkyl groups mentioned, halogen atoms, especially those mentioned, and/or trifluoromethyl groups.

Aromatic residues $R_o$ are above all phenyl residues, which can for example be substituted as indicated above.

The term hydrocarbon residues of aliphatic character is used to describe those residues of which the first member, bonded to the substituted atom, is not a member of an aromatic system. Such residues are above all aliphatic, cycloaliphatic and araliphatic residues, such as for example alkyl residues, especially lower residues of this nature, for example those mentioned, alkenyl residues, preferably lower alkenyl residues, for example allyl or methallyl residues, cycloalkyl residues, for example cycloalkyl residues corresponding to the cycloalkenyl residues mentioned, or aryl-, especially phenyl-lower alkyl residues, which contain the lower alkyl residues mentioned.

Hydrocarbon residues of aliphatic character substituted by hydroxyl groups are primarily hydroxyalkyl residues, especially γ- and above all β-hydroxy-lower alkyl residues, for example β-hydroxyethyl, γ-hydroxypropyl or β,γ-dihydroxypropyl residues. In di- or polyhydroxyalkyl residues, the hydroxy groups can also be bonded to ketal or acetal groupings by ketones and aldehydes, chiefly lower alkanones and alkanals, for example acetone or formaldehyde.

The amino groups which optionally substitute the hydrocarbon residues of aliphatic character can be unsubstituted but are preferably monosubstituted and above all disubstituted. As substituents, cycloaliphatic or araliphatic hydrocarbon residues should for example be quoted, such as those mentioned, it being possible for aromatic rings to be substituted as indicated above with regard to the residue $R_o$, but preferably aliphatic hydrocarbon residues which are optionally interrupted by hetero-atoms, such as lower alkyl residues or lower alkylene residues optionally interrupted by oxygen, sulphur or nitrogen atoms. The amino groups mentioned primarily substitute lower alkyl groups.

The hydroxyl compound of formula $R_oOH$ is preferably a lower alkanol, such as methanol, ethanol, n-propanol or iso-propanol or a butanol, a cycloalkanol, such as a cyclohexanol, for example 3,3,5-trimethylcyclohexanol, a phenyl-lower alkanol, for example benzyl alcohol or phenyl-ethanol, a lower alkanediol or alkanetriol, such as ethylene glycol or glycerine, or an amino-lower alkanol, for example a di-lower alkylamino-lower alkanol, such as β-dimethylamino-ethanol, or a lower alkanol substituted by a lower alkylene-amino group or by an oxa-, aza- or thia-lower alkyleneamino group, such as an optionally ring-alkylated pyrrolidino-, piperidino-, morpholino- or N'-lower alkyl-piperazino-lower alkanol, for example β-pyrrolidinoethanol, β-piperidinoethanol, β-morpholinoethanol or β-(N'-methyl-piperazino)-ethanol.

In the amides, the amide nitrogen atom can be unsubstituted, monosubstituted or disubstituted, for example by preferably lower hydrocarbon residues of aliphatic character which can be interrupted by hetero-atoms, such as oxygen, nitrogen or sulphur atoms and/or substituted, for example by hydroxyl, amino or mercapto groups or halogen atoms. In compounds with divalent hydrocarbon residues of aliphatic character, the word "lower" is used for those residues which do not contain more than 8 carbon atoms. As amide substituents, alkyl, alkenyl or alkylene residues may for example be mentioned, which can also be interrupted by oxygen, sulphur or nitrogen atoms and/or substituted, for example by hydroxyl, amino or mercapto groups or halogen atoms. As substituents, the following should in particular be mentioned: lower alkyl and alkenyl residues, such as for example those mentioned, lower alkylene residues, such as for example butylene-(1,4), pentylene-(1,5), hexylene-(1,6) or heptylene-(2,6), cycloalkyl or cycloalkyl-alkyl residues or corresponding residues interrupted by the hetero-atoms mentioned, such as for example lower alkoxyalkyl, alkylmercaptoalkyl or monoalkylaminoalkyl or dialkylaminoalkyl residues, such as for example 2-methoxyethyl, 2-ethoxyethyl, 3-methoxypropyl, 2-methylmercaptoethyl, or dimethyl-, methyl-ethyl or diethylamino-alkyl groups, alkyleneamino-alkyl groups or oxa-, aza- or thia-alkyleneamino-alkyl groups, wherein possible alkylene residues or oxa-, aza- or thia-alkylene residues for example are the residues mentioned above or below, or oxa-, aza- or thia-alkylene residues with 4–8 carbon atoms and 5–7 chain members, in which the hetero-atom is separated by at least 2 carbon atoms from both ends of the chain, such as 3-oxa-, 3-aza- or 3-thia-pentylene-(1,5), 3-methyl- or 3-ethyl-3-aza-hexylene-(1,6), 3-aza-hexylene-(1,6) or 4-methyl-4-aza-heptylene-(2,6), or substituted residues of this nature, such as 3-chlorethyl- or 3-hydroxyethyl-3-aza-pentylene-(1,5), or phenyl or phenyl-alkyl residues which can be unsubstituted or above all substituted in the phenyl residue as indicated for the phenyl-lower alkyl residues. The amide nitrogen atom can however also be substituted by a hydroxyl or amino group.

The amino group of the amides is accordingly especially a free, mono- or di-lower alkylated amino group, or an optionally C-lower alkylated pyrrolidino, piperidino, morpholino, thiomorpholino, piperazino, N'-lower alkylpiperazino or N'-(hydroxy-lower alkyl)-piperazino group, for example the N'-methylpiperazino group or the N'-(3-hydroxyethyl)-piperazino group, or N'-phenylpiperazino group. The expression C-lower alkylated means here, as also in what follows, that the residue in question is substituted at C-atoms by lower alkyl residues, such as those stated, and especially by alkyl residues having 1 to 3 carbon atoms.

The invention accordingly relates, for example, to compounds of the formula

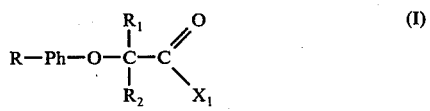

Wherein —COX$_1$ denotes a free, esterified or amidised carboxyl group, R$_1$ denotes alkyl with 5–12 carbon atoms, especially 5–10 carbon atoms and R$_2$ stands for hydrogen, R denotes a cycloaliphatic hydrocarbon residue which is unsaturated in the 1-position and is only singly unsaturated and Ph denotes ortho-, preferably, however, meta- and most particularly para-phenylene which may be substituted by 1,2 or 3 substituents selected from lower alkyl, halogen, trifluoromethyl, nitro, amino or acylamino.

The new compounds possess valuable pharmacological properties, above all a serum triglyceride-lowering action, as is found in animal experiments, for example on male rats which have fasted for 24 hours, on repeated administration of 1.0–100 mg/kg. However they also show a serum cholesterol-lowering action, as is found in normally fed male rats on repeated administration of 1.0–100 mg/kg p.o. and in dogs on repeated administration of 10 mg/kg p.o. The new compounds, however, also bring about a lowering of the liver lipids, as can be shown, for example, in male rats which have fasted for 24 hours on repeated administration of 100 mg/kg p.o. The new compounds therefore are useful as hypolipidaemic agents. They are however also useful as starting products for the manufacture of other valuable substances, especially pharmacologically active substances.

The invention relates preferably to compound of the formula I in which X$_1$ stands for a member selected from the group consisting of hydroxyl, lower alkoxy and phenyl-lower alkoxy, Ph stands for a member selected from the group consisting of para-phenylene and para-phenylene substituted by a member selected from the group consisting of lower alkyl, halogen and trifluoromethyl, R stands for a member selected from the group consisting of 1-cycloalkenyl having 4–10 ring carbon atoms and lower alkylated 1-cycloalkenyl having 4–10 ring carbon atoms, R$_2$ stand for hydrogen and R$_1$ stands for C$_{5-12}$-alkyl with a straight chain.

The invention relates especially to compounds of the formula I in which X$_1$ stands for a member selected from the group consisting of hydroxy, methoxy and ethoxy, Ph stands for a member selected from the group consisting of para-phenylene, para-phenylene substituted by methyl and para-phenylene substituted by chlorine, R stands for a member selected from the group consisting of 1-cyclopentenyl, 1-cyclohexenyl, 1-cycloheptenyl, 1-cyclooctenyl and 1-cyclononenyl, R$_1$ stands for n-alkyl having 5–12 carbon atoms and R$_2$ stands for hydrogen.

The invention relates very especially to compounds of the formula I, in which X$_1$ stands for a member selected from the group consisting of hydroxy and ethoxy, Ph stands for para-phenylene, R stands for 1-cyclohexenyl, R$_2$ stands for hydrogen and R$_1$ stands for a member selected from the group consisting of n-pentyl, n-hexyl, n-heptyl, n-octyl, n-nonyl and n-decyl.

The invention relates very especially to compounds of the formula I in which X$_1$ stands for a member selected from the group consisting of hydroxy and ethoxy, Ph stands for para-phenylene, R stands for 1-cyclooctenyl, R$_2$ stands for hydrogen and R$_1$ stands for a member selected from the group consisting of n-pentyl, n-hexyl, n-octyl and n-decyl.

The invention relates specifically to α-[p-(1-cyclohexenyl)-phenoxy]-heptanoic acid, α-[p-(1-cyclooctenyl)-phenoxy]-n-dodecanoic acid, the A-[p-(1-cyclooctenyl)-phenoxy]-n-octanoic acid and the α-[p-(1-cyclohexenyl)-phenoxy]-n-octanoic acid of the formula

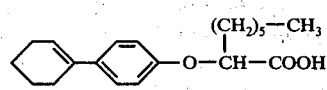

which for example shows a distinct lowering of the serum lipids in normally fed male rats on repeated administration of 2 mg/kg.

The new compounds can be manufactured according to methods which are in themselves known.

The preferred procedure is that an appropriately substituted phenol is reacted with an ester of a glycolic acid that is reactively esterified at the alcoholic hydroxyl group and is substituted in the α-position by an alkyl residue having 5–12 carbon atoms.

A reactively esterified hydroxyl group is especially a chlorine or bromine atom. The phenol is preferably used as an alkali metal salt, for example sodium or potassium salt. A perferred embodiment for example consists of reacting a suitable α-bromo-ester with the sodium salt of an appropriate phenol. The reaction can take place in the usual manner, especially in an inert, preferably anhydrous, solvent and/or at elevated temperature and/or in the presence of a strong base, for example an alkanolate, above all alkali alkanolate, such as sodium or potassium alkanolate, for example sodium ethanolate or sodium methanolate.

In resulting compounds, substituents can be introduced, modified or eliminated to suit the final substance of the invention.

Thus, for example, esterified carboxyl groups can be converted into free carboxyl groups in the usual manner, for example by hydrolysis, preferably in the presence of a strong base, such as an alkali hydroxide, for example sodium or potassium hydroxide, or in the presence of a strong acid, such as a mineral acid, such as hydrochloric or sulphuric acid.

Free or esterified carboxyl groups can also be converted into carbamyl groups in the usual manner, for example by reaction with ammonia or with amines possessing at least one hydrogen atom on the nitrogen atom, and, where appropriate, dehydration of the ammonium salt produced as an intermediate.

Free carboxyl groups can also be converted into acid halide or acid anhydride groupings in the usual manner, for example by reaction with halides of phosphorus or sulphur, such as thionyl chloride, phosphorus pentachloride or phosphorus tribromide, or with acid halides, such as chloroformic acid esters or oxalyl chloride. The acid anhydride or acid halide groups can then be converted in the usual manner, by reaction with ammonia or suitable amines or alcohols into carbamyl groups or esterified carboxyl groups, respectively.

Depending on the process conditions and starting substances, final substances which may be salt-forming are obtained in the free form or in the form of their salts, which can be converted in the usual manner into one another or into another salts. Thus acid final substances, that is to say those in which a free carboxyl group is present, are obtained in the free form or in the form of their salts with bases. Resulting free acid compounds can be converted in the usual manner, for example by reaction with appropriate basic agents, into the salts with bases, above all into therapeutically usable salts with bases, for example salts with organic amines or metal salts. Possible metal salts are above all alkali metal or alkaline earth metal salts, such as sodium, potassium, magnesium or calcium, or aluminum salts. Free acids can be liberated from the salts in the usual manner, for example by reaction with acid agents. Final substances with basic character can also be obtained in the free form or in the form of their salts. The salts of the basic final substances can be converted into the free bases in a manner which is in itself known, for example by means of alkalis or ion exchangers. From the free bases, salts can be obtained by reaction with organic or inorganic acids, especially those which are suitable for the formation of therapeutically usable salts. As such acids there may for example be mentioned: hydrogen halide acids, sulphuric acids, phosphoric acids, nitric acid, perchloric acid; aliphatic, alicyclic, aromatic or heterocyclic carboxylic or sulphonic acids, such as formic, acetic, propionic, succinic, glycollic, lactic, malic, tartaric, citric, ascorbic, maleic, hydroxymaleic or pyruvic acid; phenylacetic, benzoic, p-aminobenzoic, anthranilic, P-hydroxy-benzoic, salicylic or p-aminosalicylic acid, embonic acid, methanesulphonic, ethanesulphonic, hydroxyethanesulphonic, and ethylenesulphonic acid; halogenobenzenesulphonic, toluenesulphonic and naphthalenesulphonic acids or sulphanilic acid; methionine or tryptophane, lysine or arginine.

These and other salts can be used for the purification of the new compounds, for example by converting the free compounds into their salts, isolating these and converting them back into the free compounds. Because of the close relation-ships between the new compounds in the free form and in the form of their salts, the free compounds are, in the preceding and following texts, where appropriate also to be understood to include the corresponding salts as regards sense and purpose.

The new compounds can be in the form of optical antipodes, racemates or isomer mixture (for example racemate mixtures) depending on the choice of the starting substances and methods of working and depending on the number of asymmetric carbon atoms.

Resulting isomer mixtures (racemate mixtures can be separated in a known manner into the two stereoisomeric (diastereomeric) pure isomers (for example racemates) on the basis of the physico-chemical differences of the constituents, for example by chromatography and/or fractional crystallisation.

Resulting racemates can be resolved into the optical antipodes according to known methods, for example by recrystallisation from an optionally active solvent, with the aid of micro-organisms, or by reaction of a free carboxylic acid with an optically active base forming salts with a racemic compound and separation of the salts obtained in this manner, for example on the basis of their different solubilities, into the diastereomers; from these the antipodes can be liberated by the action of suitable agents. A particularly customary optically active base if for example the D- and L-form of cinchonine. Advantageously, the more active of the two antipodes is isolated Resulting racemates with basic compounds can furthermore be resolved into the optical antipodes by reacting the racemic compound with an optically active acid that forms salts with it and separating the salts obtained in this manner, for example on the basis of their different solubilities, into the diastereomers. From the diastereomers the antipodes can be liberated by the action of suitable agents. Particularly customary optically active acids are for example the D- and L-forms of tartaric acid, di-toluyl-tartaric acid, malic acid, mandelic acid, camphorsulphonic acid or quinic acid.

Appropriately, such starting substances are used for carrying out the reactions according to the invention as lead to the initially particularly mentioned groups of final substances and above all to the specially described or highlighted final substances.

The starting substances are know or can, if they are new, be manufactured according to methods which are in themselves known.

The phenols substituted by a cycloaliphatic hydrocarbon residue which is unsaturated in the 1-position, which are used as preferred starting substances, can be manufactured by reacting a suitable cyclic ketone with a lower alkoxyphenyl Grignard compound, splitting off water, and hydrolysing the lower alkoxy group, preferably by treatment with pyridine hydrochloride.

The new compounds can for example be employed in the form of pharmaceutical preparations in which they are present in the free form or optionally in the form of their salts, especially of the therapeutically usable alkali metal salts, mixed with a pharmaceutical, organic or inorganic, solid or liquid excipient which is for example suitable for enteral or parenteral administration. Possible substances for the formation of the latter are those which do not react with the new compounds, such as for example water, gelatine, lactose, starch, stearyl, alcohol, magnesium stearate, talc, vegetable oils, benzyl alcohols, gum, propylene glycols, white petroleum jelly or other medicinal excipients. The pharmaceutical preparations can for example be in the form of tablets, dragees, capsules or suppositories, or in a liquid form as solutions (for example as an elixir or syrup), suspensions or emulsions. They are optionally sterilised and/or contain auxiliary substances, such as preservatives, stabilisers, wetting agents or emulsifiers, solubilising agents or salts for regulating the osmotic pressure or buffers. They can also contain other therapeutically valuable substances. The pharmaceutical preparations are obtained according to customary methods.

The invention is described in more detail in the examples which follow.

EXAMPLE 1

To 0.73 g of sodium in 40 ml of absolute ethanol are added dropwise with stirring initially 5.0 g of p-(1-cyclohexenyl)-phenol in a small amount of absolute ethanol, then 7.3 g of 2-bromo-n-heptanoic acid ethyl ester, and the reaction mixture is stirred continuously overnight at 50° C. The sodium bromide that has formed is filtered off, the residue evaporated to dryness in vacuo and the evaporated residue partitioned between either and 2N sodium hydroxide solution at 0° C. The ether phases are washed until neutral, dried over sodium sulphate and evaporated in vacuo. The evaporation residue contains the oily α-[p-(1-cyclohexenyl)-phenoxyl]-n-heptanoic acid ethyl ester of the formula

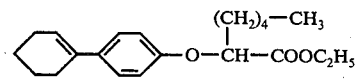

The p-(1-cyclohexenyl)-phenol used as starting material in this Example can be manufactured as follows:

To a suspension of 72 g of magnesium chips (which have been washed with chloroform and activated with iodine) in 1000 ml of absolute tetrahydrofurane is added tropwise with stirring a solution of 374 g of p-bromanisol in 600 ml of absolute tetrahydrofuran in such a way that it is possible to gently maintain the Grignard reaction that has commenced. On completion of addition, the reaction mixture is stirred for a further 1½ hours at 60° C, cooled to 20° C and treated dropwise with 294 g of cyclohexanone, care being taken that the temperature does not rise above 30° C. The reaction mixture is subsequently allowed to continue to react for 1 hour at the same temperature, then evaporated in vacuo. The residue is treated with ice and approx. 1600 ml of saturated ammonium chloride solution and extracted with ether. The solutuion is dried over sodium sulphate and evaporated in vacuo to yield an oily residue. After distillation from a Vigreux flask, the P-(1-hydroxy-cyclohexyl)-anisol is obtained, which boils at 165°-167° C (11 mm Hg).

229 Grams of this compounds are dissolved in 1100 ml of glacial acetic acid, this mixture is treated with 500 ml of 2N hydrochloric acid and the solution heated for 1 hour to 100° C. The reaction mixture is cooled to 20° C and upon addition of water, extracted with ether. The ethereal extracts are washed three times with 2N sodium hydrogen carbonate solution, dried over sodium sulphate and evaporated in vacuo. After fractionated distillation from a Claisen flask, the p-(1-cyclohexenyl)-anisol is obtained, which boils at 158°-160° C (14 mm Hg).

56.5 Grams of p-(1-cyclohexenyl)-anisol and 125 g of pyridine-hydrochloride are thoroughly mixed and heated for 3 hours in an atmosphere of nitrogen to 180° C. The reaction mixture is cooled to room temperature, treated with water and extracted with 3 × 400 ml of benzene. The benzene extracts are washes with 3 × 300 ml of water, dried over sodium sulphate and evaporated in vacuo. The solid residue yields the crude p-(1-cyclohexenyl)-phenol (m.p. 115–119° C), which can be purified by recrystallisation from benzene and then melts at 120°-122° C.

EXAMPLE 2

A solution of 7.7 g of α-[p-(1-cyclohexenyl)-phenoxy]-n-heptanoic acid ethyl ester in 100 ml of ethanol and 70 ml of 2N sodium hydroxide solution is left to stand overnight at room temperature. The bulk of the solvent is then removed in vacuo, the pH adjusted to 3 by adding concentrated by hydrochloric acid, and the residue extracted with ether. The ether phase is washed until neutral, dried over sodium sulphate and evaporated to dryness in vacuo. The residue is crystallised from petroleum ether to yield the α-[p-(1-cyclo-hexenyl)-phenoxy]-n-heptanoic acid of the formula

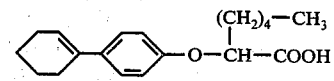

which melts at 78-80° C.

EXAMPLE 3

To 0.73 g of sodium in 40 ml of absolute ethanol are added dropwise with stirring initially 5.0 g of p-(1-cyclohexenyl)-phenol in a small amount of absolute ethanol, then 7.3 g of 2-bromo-n-octonoic acid ethyl ester, and the reaction mixture is stirred continuously overnight at 50°C. The sodium bromide that has formed is filtered off, the residue evaporated in vacuo and the evaporation residue partitioned between ether and 2N sodium hydroxide solution at 0° C. The ether phases are washed until neutral, dried over sodium sulphate and evaporated in vacuo. The evaporation residue contains the oily α-[p-(1-cyclohexenyl)-phenoxy]-n-octanoic acid ethyl ester of the formula

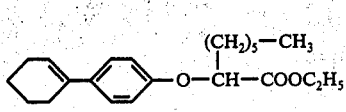

EXAMPLE 4

A solution of 7.5 g of α-[p-(1-cyclohexenyl)-phenoxy]-n-octanoic acid ethyl eter in 100 ml of ethanol and 70 ml of 2N sodium hydroxide solution is left to stand overnight at room temperature. The bulk of the solvent is evaporated in vacuo, the pH adjusted to 3 by adding concentrated hydrochloric acid, and the residue extracted with ether. The ether phase is washed until neutral, dried over sodium sulphate and evaporated in vacuo to dryness. The residue is crystallised from pentane to yield the α-[p-(1-cyclohexenyl)-phenoxyl]-n-octanoic acid of the formula

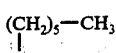

which melts at 70°–71° C.

EXAMPLE 5

To 2.1 g of sodium in 180 ml of absolute ethanol are added with stirring 15.0 g of p-(1-cyclooctenyl)-phenol. After stirring has continued for a further 30 minutes, 28.5 g of 2-bromo-heptanoic acid ethyl ester are slowly added dropwise to this solution and the mixture is maintained at 50° C for 24 hours. Upon removal of the solvent in vacuo, the residue is partitioned at 0° C between ether and 2N sodium hydroxide solution. The organic phase is washed until neutral, dried over sodium sulphate and evaporated in vacuo, to yield the oily α-[p-(1-cyclooctenyl)-phenoxy]-heptanoic acid ethyl ester of the formula

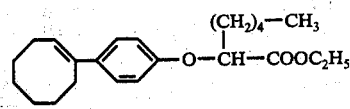

The p-(1-cyclooctenyl)-phenol used in this Example as starting material can be manufactured as follows:

To a vigorously stirred suspension of 19.5 g of magnesium chips (which have been washed with chloroform and activated with iodine) in 800 ml of absolute tetrahydrofuran is added in increments a solution of 131 g of p-bromanisol in 200 ml of absolute tetrahydrofuran in such a way that it is possible to maintain gently the Crignard reaction. The reaction mixture is allowed to continue to react for 1 hour, cooled to 15° C and treated dropwise with 88 g of cyclooctanone. After the reaction mixture has been stirred for a further 5 hours, it is treated with ice and with saturated ammonium chloride solution. The whole mixture is extracted with ether, the ether layers are washed with water, dried over sodium sulphate and evaporated in vacuo. During distillation under a high vacuum, water is split off from the oily residue to thus yield the p-(1-cyclooctenyl)-anisol, which boils at 115°–118° C (0.05mm Hg).

80 Grams of p-(1-cyclooctenyl)-anisol and 175 g of pyridine-hydrochloride are thoroughly mixed and heated for 4 hours under nitrogen to 180° C. The mixture is cooled, treated with water and extracted with benzene. The benzene extracts are shaken with 3×100 ml of N-sodium hydroxide solution. The alkaline phase is acidified with 2N hydrochloric acid and extracted with ether. The ether solution is dried over sodium sulphate and evaporated. The residue is recrystallised from benzene-petroleum ether to yield the p-(1-cyclooctenyl)-phenol (m.p. 95°–97° C).

EXAMPLE 6

To 33 g of α-[p-(1-cyclooctenyl)-phenoxy]-heptanoic acid ethyl ester in 120 ml of ethanol are added 120 ml of 2N sodium hydroxide solutuion and the mixture is stirred for 1½ hours at room temperature. The reaction mixture is then evaporated to dryness in vacuo and the residue partitioned between N hydrochloric acid and ether. The organic phase is washed until neutral, dried over sodium sulphate and evaporated to dryness in vacuo. The residue is crystallised from pentane to yield the 2-[p-(1-cyclooctenyl)-phenoxy]-heptanoic acid of the formula

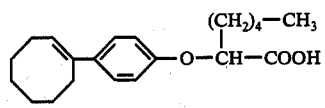

(m.p. 57°–60° C; b.p. $_{0.04}$ 185°–188° C.

EXAMPLE 7

To 2.1 g of sodium in 150 ml of absolute ethanol are added with stirring 15 g of p-(1-cyclooctenyl)-phenol. After stirring has continued for a further 30 minutes, 30 g of 2-bromo-octanoic acid ethyl ester are slowly added dropwise to this solution and the mixture is maintained at 50° C for 24 hours. After the solvent has been removed in vacuo the residue is partitioned at 0° C between ether and 2N sodium hydroxide solutuion. The organic phase is washed until neutral, dried over sodium sulphate and evaporated in vacuo, to thus yield the oily α-[p-cyclooctenyl)-phenoxy]-octanoic acid ethyl ester of the formula

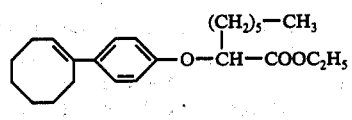

EXAMPLE 8

To 34 g of α-[p-(1-cyclooctenyl)-phenoxy]-octanoic acid ethyl ester in 120 ml of ethanol are added 120 ml of 2N sodium hydroxide solution and the mixture is stirred for 1½hours at room temperature. The reaction mixture is then evaporated to dryness in vacuo and the residue partitioned between N-hydrochloric acid and ether. The organic phase is washed until neutral, dried over sodium sulphate and evaporated to dryness in vacuo. The residue is distilled at 0.07 mm/205°–210° C. The distillate is crystallised from pentane at 0° C to yield the α-[p-(1-cyclooctenyl)-phenoxy]-octanoic acid of the formula

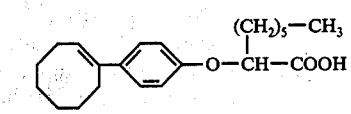

which melts at 55°–57° C.

EXAMPLE 9

To 2.1 g of sodium in 100 ml of absolute ethanol are added stirring 15 g of p-(1-cyclooctenyl)-phenol. After stirring has continued for a further 30 minutes, 31.5 g of 2-bromo-decanoic acid ethyl ester are slowly added dropwise to this solution and the mixture is maintained at 50° C for 24 hours. After the solvent has been removed in vacuo, the residue is partitioned at 0° C between either and 2N sodium hydroxide solution. The organic phase is washed until neutral, dried over sodium sulphate and evaporated in vacuo, to thus yield the oily α-[p-(1-cyclooctenyl)-phenoxy]-decanoic acid ethyl ester of the formula

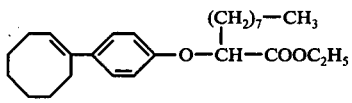

EXAMPLE 10

To 37 g of α-[p-(1-cyclooctenyl)-phenoxy]-decanoic acid ethyl ester in 150 ml of ethanol are added 150 ml of 2N sodium hydroxide solution and the mixture is stirred for 2 hours at room temperature. The reaction mixture is then evaporated to dryness in vacuo and the residue partitioned between N hydrochloric acid and ether. The organic phases are washed until neutral, dried over sodium sulphate and evaporated to dryness in vacuo. The residue is distilled under a high vacuum. The distillate contains the α-[p-(1-cyclooctenyl)-phenoxy]-decanoic acid of the formula

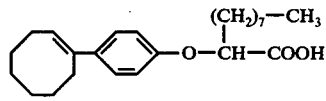

(b.p. 216°–219° C/ 0.05 mm).

EXAMPLE 11

To 2.1 g of sodium in 100 ml of absolute ethanol are added with stirring 15 g of p-(1-cyclooctenyl)-phenol. After stirring has continued for a further 30 minutes, 35 g of 2-bromo-dodecanoic acid ethyl ester are slowly added dropwise to this solution and the mixture is maintained at 50° C for 24 hours. After the solvent has been removed in vacuo, the residue is partitioned at 0° C between ether and 2N sodium hydroxide solution. The organic phase is washed until netural, dried over sodium sulphate and evaporated in vacuo, to thus yield the oily α-p-(1-cyclooctenyl)-phenoxy-dodecanoic acid ethyl ester of the formula

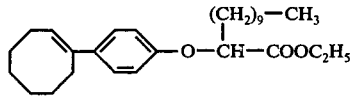

EXAMPLE 12

To 38 g of α-[p-(1-cyclooctenyl)-phenoxy]-dodecanoic acid ethyl ester in 150 ml of ethanol are added 150 ml of 2N sodium hydroxide solution and the mixture is stirred for 2 hours at room temperature. The reaction mixture is then evaporated to dryness in vacuo and the residue partitioned between N hydrochloric acid and ether. The organic phases are washed until neutral, dried over sodium sulphate and evaporated to dryness in vacuo. The residue is distilled under a high vacuum at 0.05 mm and 235°–239° C. The distillate is cyrstallised from pentane to yield the α-[p-(1-cyclooctenyl)-phenoxy]-dodecanoic acid of the formula

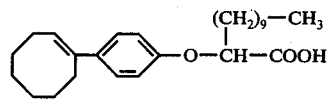

which melts at 45°–48° C.

EXAMPLE 13

To a solution of 2.4 g of sodium in 100 ml of absolute ethanol are added initially 15 g of p-(1-cyclohexenyl)-phenol in a small amount of absolute ethanol at room temperature under anhydrous conditions and with stirring. 34 Grams of α-bromo-nonanoic acid ethyl ester are then added dropwise and the reaction mixture is stirred for 24 hours at 50° C. The ethanol is subsequently stripped off in vacuo and the residue is partitioned between water and ice-cold N sodium hydroxide solution. The organic phase is washed until neutral, dried over sodium sulphate and concentrated in vacuo. The residue yields the crude α-[p-(1-cyclohexyl)-phenoxy]-nonanoic acid ethyl ester of the formula

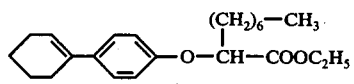

in the form of an oil.

EXAMPLE 14

To 38 g of α-[p-(1-cyclohexenyl)-phenoxy]-nonanoic acid ethyl ester in 150 ml of ethanol are added 150 ml of 2N sodium hydroxide solution and the mixture is stirred at room temperature for 2 hours. The ethanol is stripped off in vacuo and the residue partitioned between 2N hydrochloric acid and ether. The organic phase is washed until neutral, dried over sodium sulphate and evaporated to dryness. Distilation of the residue at 0.04 mm yields in the fraction boiling at 173°–176° C the α-[p-(1-cyclohexenyl)-phenoxy]-nonanoic acid of the formula

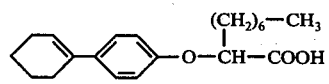

(m.p. 61°–63° C).

EXAMPLE 15

To a solutuion of 1.6 g of sodium in 100 ml of absolute ethanol are added initially 10 g of p-(1-cyclohexenyl)-phenol in a small amount of absolute ethanol at room temperature under anhydrous conditions and with stirring. 26 Grams of α-bromo-dodecanoic acid ethyl ester are then added dropwise and the mixture is maintained at 50° C for 24 hours. The ethanol is subsequently stripped off in vacuo and the residue is partitioned between water and ice-cold N sodium hydroxide solutuion. The organic phase is washed until neutral, dried over sodium sulphate and concentrated in vacuo. The residue yields the crude α-[p-(1-cyclohexenyl)-phenoxy]-dodecanoic acid ethyl ester of the formula

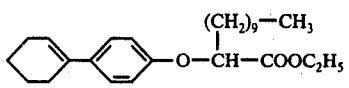

in the form of an oil.

EXAMPLE 16

To 23.5g of α-[p-(1-cyclohexenyl)-phenoxy]-dodecanoic acid ethyl ester in 150 ml of ethanol are added 100 ml of 2N sodium hydroxide solution and the mixture stirred for 2 hours at room temperature. The ethanol is stripped off in vacuo and the residue partitioned between 2N hydrochloric acid and ether. The organic phase is washed until neutral, dried over sodium sulphate and evaporated to dryness. Distillation of the residue at 0.04 mm yields in the fraction boiling at 190°-197° C the α-[p-(1-cyclohexenyl)-phenoxy]-dodecanoic acid of the formula

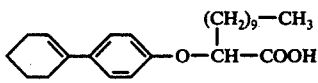

(m.p. 70°-72° C).

EXAMPLE 17

To a solution of 1.6 g of sodium in 100 ml of absolute ethanol, 10 g of p-(1-cyclohexenyl)-phenol in a small amount of absolute ethanol are added at room temperature under anhydrous conditions and with stirring. 25.2 Grams of α-bromo-undecanoic acid ethyl ester are then added dropwise. and the reaction mixture is stirred for 24 hours at 50° C. The ethanol is subsequently stripped off in vacuo and the residue is partitioned between water and ice-cold N solution hydroxide solution. The organic phase is washed until neutral, dried over sodium sulphate and concentrated in vacuo. The residue yields the crude α-[p-(1-cyclohexenyl)-phenoxy]-undecanoic acid ethyl ester of the formula

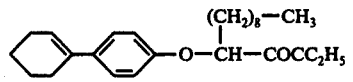

in the form of an oil.

EXAMPLE 18

To 27 g of α-[p-(1-cyclohexenyl)-phenoxy]-undecanoic acid ethyl ester in 150 ml of ethanol are added 100 ml of 2N sodium hydroxide solution and the mixture stirred for 2 hours at room temperature. The ethanol is stripped off in vacuo and the residue partitioned between 2N hydrochloric acid and ether. The organic phase is washed until neutral, dried over sodium sulphate and evaporated to dryness. Distillation of the residue at 0.04 mm yields in the fraction boiling at 185°-190° C the α-[p-(1-cyclohexenyl)-phenoxy]-undecanoic acid of the formula

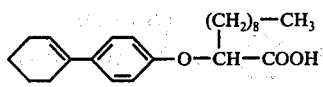

(m.P. 70°-73° C).

EXAMPLE 19

To a solution of 1.6g of sodium in 100 ml of absolute ethanol, 10 g of p-(1-cyclohexenyl)-phenol in a small amount of absolute ethanol are added at room temperature under anhydrous conditions and with stirring. 10 g of α-bromo-decanoic acid ethyl ester are then added dropwise and the reaction mixture is stirred up for 24 hours at 50° C. The ethanol is subsequently stripped off in vacuo and the residue is partitioned between water and ice-cold N-sodium hydroxide solution. The organic phase is washed until neutral, dried over sodium sulphate and concentrated in vacuo. The residue yields the crude α-[p-(1-cyclohexenyl)-phenoxy]-decanoic acid ethyl ester of the formula

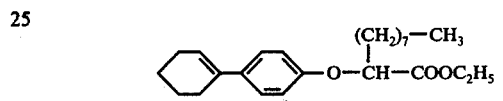

in the form of an oil.

EXAMPLE 20

To 22.7 g of α-[p-(1cyclohexenyl)-phenoxy]-decanoic acid ethyl ester in 120 ml of ethanol are added 100 ml of 2N sodium hydroxide solution and the mixture stirred for 3 hours at room temperature. The ethanol is stripped off in vacuo and the residue partitioned between 2N hydrochloric acid and ether. The organic phase is washed until neutral, dried over sodium sulphate and evaporated to dryness. Distillation of the residue at 0.03 mm yields in the fraction boiling at 175°-180° C the α-[p-(1-cyclohexenyl)-phenoxy]-decanoic acid of the formula

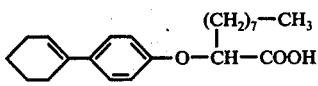

(m.p. 75°-78° C).

EXAMPLE 21

To a solution of 5 g of isopropylamine and 5 ml of triethylamine in 100 ml of absolute tetrahydrofuran is slowly added dropwise with stirring at −5° C a solution of 13 g of α-[p-(1-cyclohexenyl)-phenoxy]-heptanoic acid chloride in 25 ml of absolute tetrahydrofuran. The reaction mixture is left to stand for 5 hours at room temperature, then evaporated in vacuo to dryness. The residue is partitioned between methylene chloride and 2N hydrochloric acid. The organic phase is washed with saturated sodium bicarbonate solution and water, dried over sodium sulphate and evaporated in vacuo. The residue yields the crude α-[p-(1-cyclohexenyl)-phenoxy]-heptanoic acid isopropylamide of the formula

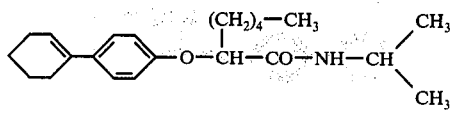

(m.p. 86°–88° C after recrystallisation from petroleum ether).

The α-[p-(1-cyclohexenyl)-phenoxy]-heptanoic acid chloride used as starting material can be obtained as follows:

To a suspension of 12 g of the sodium salt of α-[p-(1-cyclohexenyl)-phenoxy]-heptanoic acid in 200 ml of absolute benzene are added with stirring at 5°C 25 g of oxalyl chloride. The mixture is continuously stirred overnight at room temperature, then evaporated to dryness in vacuo. The residue is dissolved in 200 ml of absolute benzene are added with stirring at 5° C 25 g of oxalyl chloride. The mixture is continuously stirred overnight at room temperature, then evaporated to dryness in vacuo. The residue is dissolved in 200 ml of absolute benzene and filtered under anhydrous conditions. The filtrate is evaporated to dryness in vacuo. The residue yields the crude α-[p-(1-cyclohexenyl)-phenoxy]-heptanoic acid chloride, which is used directly for further processing.

EXAMPLE 22

5.0 g of p-(1-cycloheptenyl)-phenol in a little absolute ethanol, followed by 7.3 g of 2-bromo-n-nonanoic acid ethyl ester, are added dropwise, whilst stirring, to 0.73 g of sodium in 40 ml of absolute ethanol. The mixture is stirred further overnight at 50° C. the sodium bromide formed is filtered off, the filtrate is evaporated to dryness in vacuo and the evaporation residue is partitioned between ether and 2 N sodium hydroxide solution at 0° C. The ether phases are washed until neutral, dried over sodium sulphate and concentrated by evaporation in vacuo. The evaporation residue contains oily α-[p-(cycloheptenyl)-phenoxy]-n-nonanoic acid ethyl ester of boiling point 150° C/0.06 mm Hg.

EXAMPLE 23

A solution of 7.5 g of α-[p-(1-cycloheptenyl)-phenoxy]-n-nonanoic acid ethyl ester in 100 ml of ethanol and 70 ml of 2 N sodium hydroxide solution is left to stand overnight at room temperature. The bulk of the solvent is then removed in vacuo, the pH is adjusted to 3 with concentrated hydrochloric acid and the mixture is extracted with ether. The ether phase is washed until neutral, dried over sodium sulphate and evaporated to dryness in vacuo. The residue is distilled in a high vacuum, whereupon α-[p-(1-cycloheptenyl)-phenoxy]-n-nonanoic acid of boiling point 190°C/0.05 mm Hg passes over.

EXAMPLE 24

15 g of p-(1-cycloheptenyl)-phenol are added to 2.1 g of sodium in 100 ml of absolute ethanol, whilst stirring. After stirring for a further 30 minutes, 31.5 g of 2-bromo-decanoic acid ethyl ester are slowly added dropwise to this solution, and the mixture is warmed to 50° C for 24 hours. After removing the solvent in vacuo, the residue is partitioned between ether and 2 N sodium hydroxide solution at 0° C. The organic phase is washed until neutral, dried over sodium sulphate and concentrated by evaporation in vacuo. This gives α-[p-(1-cycloheptenyl)-phenoxy]-decanoic acid ethyl ester of boiling point 180° C/0.05 mm Hg.

EXAMPLE 25

150 ml of 2 N sodium hydroxide solution are added to 37 g of α-[p-(1-cycloheptenyl)-phenoxy]-decanoic acid ethyl ester in 150 ml of ethanol and the mixture is stirred for 2 hours at room temperature. It is then evaporated to dryness in vacuo and the residue is partitioned between 1 N hydrochloric acid and ether. The organic phases are washed until neutral, dried over sodium sulphate and evaporated to dryness in vacuo. The residue is distilled in a high vacuum. The distillate contains α-[p-(1-cycloheptenyl)-phenoxy]-decanoic acid of boiling point 190° C/0.05 mm Hg, in the fraction boiling at 175°–190° C/0.05 mm Hg.

EXAMPLE 26

10 g of p-(1-cycloheptenyl)-phenol in a little absolute ethanol are first added to a solution of 1.6 g of sodium in 100 ml of absolute ethanol, which is stirred at room temperature whilst excluding water; 25.2 g of α-bromo-undecanoic acid ethyl ester are then added dropwise, the mixture is left at 50°C for 24 hours, the ethanol is removed in vacuo and the residue is partitioned between ether and ice-cold 1 N sodium hydroxide solution. The organic phase is washed until neutral, dried over sodium sulphate and concentrated by evaporation in vacuo. Crude α-[p-(1-cycloheptenyl)-phenoxy]-undecanoic acid ethyl ester boiling at 160° C/0.06 mm Hg is obtained in the evaporation residue.

EXAMPLE 27

100 ml of 2N sodium hydroxide solution are added to 27 g of α-[p-(1-cycloheptenyl)-phenoxy]-undecanoic acid ethyl ester in 150 ml of ethanol and the mixture is stirred for 2 hours at room temperature. The ethanol is removed in vacuo and the residue is partitioned between 2 N hydrochloric acid and ether. The organic phases are washed until neutral, dried over sodium sulphate and concentrated by evaporation in vacuo. Distillation of the residue at 0.04 mm gives α-[p-(1-cycloheptenyl)-phenoxy]-undecanoic acid, of melting point 79°–81° C (from n-hexane), in the fraction boiling at 185°–190° C.

EXAMPLE 28

Analogously to the process described in Example 1, 11.5 g of p-(1-cycloheptenyl)-phenol and 26.4 g of 2-bromooctanoic acid ethyl ester give α-[p-(1-cycloheptenyl)-phenoxy]-octanoic acid ethyl ester as a colourless oil of boiling point 155°–160° C/0.04 mm Hg.

EXAMPLE 29

Analogously to the process described in Example 2, 13 g of α-[p-(1-cycloheptenyl)-phenoxy]-octanoic acid ethyl ester, on alkaline saponification with 27 ml of 2 N sodium hydroxide solution in 130 ml of ethanol, give α-[p-(1-cycloheptenyl)-phenoxy]-octanoic acid of melting point 59°–60° C (from cold hexane).

EXAMPLE 30

Analogously to the process described in Example 1, 13.2 g of p-(1-cycloheptenyl)-phenol and 28 g of 2-bromoheptanoic acid ethyl ester give α-[p-(1-cycloheptenyl)-phenoxy]-heptanoic acid ethyl ester, of boiling point 160°–164° C, as a colourless oil.

EXAMPLE 31

Analogously to the process described in Example 2, 13 g of α-[p-(1-cycloheptenyl)-phenoxy]-heptanoic acid ethyl ester and 29 ml of 2 N sodium hydroxide solution in 130 ml of ethanol give α-[p-(1-cycloheptenyl)-phenoxy]-heptanoic acid of melting point 69°-71° C (from cold hexane).

EXAMPLE 32

In an analogous as described in Examples 1-46 for example also the following corresponds can be prepared α-[4(1-cyclohexenyl)-phenoxy]-n-tridecanoic acid,
α-[4-(1-cyclohexenyl)-phenoxy]-n-tridecanoic acid ethyl ester,
α-[4-(1-cyclohexenyl)-phenoxy]-n-tetradecanoic acid,
α-[4-(1-cyclohexenyl)-phenoxy]-n-tetradecanoic acid ethyl ester,
α-[p-(1-cyclooctenyl)-phenoxy]-n-nonanoic acid,
α-[p-(1-cyclooctenyl)-phenoxy]-n-nonanoic acid ethyl ester,
α-[p-(1-cyclooctenyl)-phenoxy]-n-undecanoic acid,
α-[p-(1-cyclooctenyl)-phenoxy]-n-undecanoic acid ethyl ester,
α-[p-(1-cyclooctenyl)-phenoxy]-n-tridecanoic acid,
α-[p-(1-cyclooctenyl)-phenoxy]-n-tridecanoic acid ethyl ester,
α-[p-(1-cyclooctenyl)-phenoxy]-n-tetradecanoic acid,
α-[p-(1-cyclooctenyl)-phenoxy]-n-tetradecanoic acid ethyl ester.

EXAMPLE 33

Tablets having a content of 0.05 g of active substance are prepared as follows:

| Constituents (for 1000 tablets) | |
| --- | --- |
| Sodium salt of α-[p-(1-cyclohexenyl)-phenoxy]-n-octanoic acid or of α-[p-(1-Cycloheptenyl)-phenoxy]-n-heptanoic acid | 50.0 g |
| Lactose | 67.7 g |
| Cornstarch | 30.0 g |
| Stearic acid | 1.0 g |
| Magnesium stearate | 1.0 g |
| Silica gel | 0.3 g |
| Purified water | q.s. |

All the pulverulent substances are individually passed through a sieve with a 3 mm mesh and thoroughly mixed. From one third of the starch and an appropriate amount of water, one third of the lactose and a further one third of the starch, if necessary with the addition of more water, a paste is prepared for the granulation of the active substance. The granulate is dried for 16 hours at 35° C, passed through a sieve with a 1.2 mm mesh, and mixed with the remainder of the starch, with stearic acid, magnesium stearate and silica gel and pressed into tablets each weighing 0.15 g (7.0 mm diameter) which have a breaking groove.

We claim:

1. A member selected from the group consisting of compounds of the formula

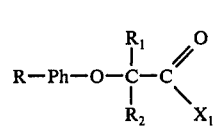

in which $X_1$ stands for a member selected from the group consisting of hydroxyl, lower alkoxy and phenyl-lower alkoxy, Ph stands for a member selected from the group consisting of para-phenylene and para-phenylene substituted by a member selected from the group consisting of lower alkyl, halogen and trifluoromethyl, R stands for 1-cycloalkenyl having 6-8 ring carbon atoms $R_2$ stands for hydrogen and $R_1$ stands for $C_{5-12}$-alkyl with straight-chain.

2. A product as claimed in claim 1, in which $X_1$ stands for a member selected from the group consisting of hydroxy, methoxy and ethoxy, Ph stands for a member selected from the group consisting of para-phenylene, para-phenylene substituted by methyl and para-phenylene substituted by chlorine, R stands for 1-cycloheptenyl, $R_1$ stands for n-alkyl having 5-12 carbon atoms and $R_2$ stands for hydrogen.

3. A product as claimed in claim 1, in which $X_1$ stands for a member selected from the group consisting of hydroxy and ethoxy, Ph stands for para-phenylene, R stands for 1-cyclohexenyl, $R_2$ stands for hydrogen and $R_1$ stands for a member selected from the group consisting of n-pentyl, n-hexyl, n-heptyl, n-octyl, n-nonyl and n-decyl.

4. A product as claimed in claim 1, in which $X_1$ stands for a member selected from the group consisting of hydroxy and ethyxy, Ph stands for para-phenylene, R stands for 1-cyclooctenyl, $R_2$ stands for hydrogen and $R_1$ stands for a member selected from the group consisting of n-pentyl, n-hexyl, n-octyl and n-decyl.

5. A compound as claimed in claim 1, said compound being α-[para-(1-cyclohexenyl)-phenoxy]-n-heptanoic acid or a salt thereof.

6. A compound as claimed in claim 1, said compound being α-[para-(P1-cyclohexenyl)-phenoxy]-n-octanoic acid or a salt thereof.

7. A compound as claimed in claim 1, said compound being α-[para-(1-cyclooctenyl)-phenoxy]-n-octanoic acid or a salt thereof.

8. A compound as claimed in claim 1, said compound being α-[para-(1-cyclohexenyl)-phenoxy]-n-nonanoic acid or a salt thereof.

9. A compound as claimed in claim 1, said compound being α-[para-(1-cyclohexenyl)-phenoxy]-n-undecanoic acid or a salt thereof.

10. A compound as claimed in claim 1, said compound being α-[para-(1-cycloheptenyl)-phenoxy]-n-hetanoic acid or a salt thereof.

11. A compound as claimed in claim 1 said compound being α-[para-(1-cycloheptenyl)-phenoxy]-n-nonanoic acid or a salt thereof.

12. A compound as claimed in claim 1, said compound being α-[para-(1-cycloheptenyl-phenoxy]-n-undecanoic acid or a salt thereof.

13. A compound as claimed in claim 1 said compound being α-[para-(1-cyclooctenyl)-phenoxy]-n-heptanoic acid or a salt thereof.

14. A compound as claimed in claim 1, said compound being α-[para-(1-cyclooctenyl)-phenoxy]-n-decanoic acid or a salt thereof.

15. A hypolipidaemic pharmaceutical preparation comprising a hypolipidaemically effective amount of a compound as claimed in claim 1 together with a pharmaceutical excipient.

* * * * *